United States Patent

Kuriyama et al.

[11] Patent Number: 6,069,139
[45] Date of Patent: *May 30, 2000

[54] METHOD AND COMPOSITION FOR PROPHULAXIS AND TREATMENT OF RETINAL DISEASES

[75] Inventors: Hiroshi Kuriyama, Toyonaka; Hiroaki Naka; Mitsunori Waki, both of Kobe, all of Japan

[73] Assignee: Senju Pharmaceutical Company, Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/972,036

[22] Filed: Nov. 17, 1997

Related U.S. Application Data

[63] Continuation of application No. 08/437,468, May 9, 1995, abandoned.

[30] Foreign Application Priority Data

May 10, 1994 [JP] Japan .................................. 6-095939

[51] Int. Cl.⁷ .................................................. A61K 31/665
[52] U.S. Cl. ........................................... 514/100; 514/912
[58] Field of Search ...................... 514/100, 912

[56] References Cited

FOREIGN PATENT DOCUMENTS 0430045   6/1991   European Pat. Off. .

*Primary Examiner*—Zohreh Fay
*Attorney, Agent, or Firm*—Millen, White, Zelano & Branigan, P.C.

[57] ABSTRACT

A pharmaceutical composition is provided for prophylaxis and treatment of a retinal disease in a human comprising (a) a compound of the formula I:

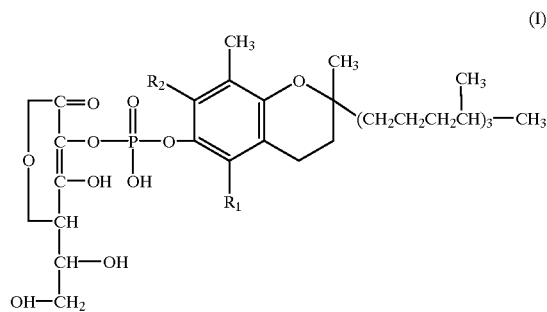

wherein $R_1$ and $R_2$ independently from each other denote hydrogen or methyl group, or a pharmacologically acceptable salt thereof, and (b) a pharmacologically acceptable carrier therefor. Also provided are a method for prophylaxis and treatment of a retinal disease comprising administering such a compound and a use of such a compound for preparing a pharmaceutical composition for the same purpose.

2 Claims, 3 Drawing Sheets

METHOD AND COMPOSITION FOR PROPHULAXIS AND TREATMENT OF RETINAL DISEASES

This application is a continuation, of application Ser. No. 08/437,468, filed May 9, 1995, now abandoned.

BACKGROUND OF THE INVENTION

The present invention relates to a pharmaceutical composition for prophylaxis and treatment of retinal diseases. More specifically, the present invention relates to a pharmaceutical composition and a method for prophylaxis and treatment of retinal diseases which contains a diester of phosphoric acid with ascorbic acid and tocopherol or a pharmacologically acceptable salt of the diester.

A variety of retinal diseases are known. Examples of such retinal disorders include:

(a) vascular disorders and inflammatory or degenerative lesions of the retina resulting from one or more systemic diseases such as diabetes mellitus, hypertension, arteriosclerosis, anemia, leukemia, certain connective tissue diseases (e.g., systemic lupus erythematosus, seeroderma), and some kinds of congenital metabolic abnormalities (e.g., Tay-Sachs' disease, Vogt-Spielmeyer disease,); and (b) diseases localized in the retina including such kinds of retinal vascular disorders (e.g., retinopathy of prematurity, retinal vein occlusion, retinal artery occlusion, and retinal periphlebitis), retinal inflammation or degeneration resulting from retinal detachment or trauma, retinal degenerative diseases accompanying aging (e.g., senile disciform macular degeneration), and congenital retinal degenerative diseases.

In order to treat a patient for his or her retinal disease, and where it has resulted from one or more systemic diseases, respective systemic causal therapies may be given to the patient, such as administration of hypotensive drugs for hypertension, and hypoglycemic agents for diabetes mellitus, for example. These therapies, however, do not ensure alleviation of relating retinal diseases. In addition, systemic causal therapies sometimes are unsuccessful or unavailable for autoimmune diseases or congenital metabolic abnormalities. Thus, therapies are necessary that are targeted to act on retinal lesions directly. Thus, for example, vasodilators, drugs directed to fortify vascular walls, or thrombolytic agents are applied in the cases of retinal vascular lesions observed in diabetes mellitus, hypertension, retinal vein occlusion, or retinal artery occlusion. However, these drug therapies are not sufficient in their efficacy and, consequently, surgical treatment is often required in practice.

It has been suspected (i) that there might be involved ischemia and hypoxia and resultant peroxidation reactions in the onset and/or advancement of each of the above retinal diseases, and (ii) that excess light might be a risk factor of these diseases, considering the specificity of the retinal function which evokes vision upon the reception of light.

Upon this background, the inventors of the present invention have pursued an investigation in search of a useful drug for treatment of retinal diseases. By studying pharmacological effects of diesters of phosphoric acid, the inventors have found that certain diesters of phosphoric acid with ascorbic acid and tocopherol, are useful as prophylactic and therapeutic agents for a variety of retinal diseases as mentioned above. The present invention have thus been accomplished on the basis of this finding.

SUMMARY OF THE INVENTION

The invention provides a pharmaceutical composition for prophylaxis and treatment of a retinal disease in a human comprising (a) a compound of the formula I:

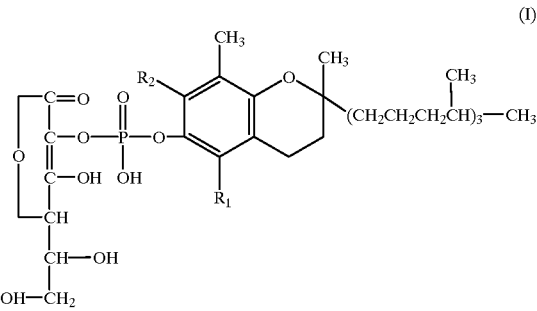

wherein $R_1$ and $R_2$ independently from each other denote hydrogen or methyl group, or a pharmacologically acceptable salt thereof, and (b) a pharmacologically acceptable carrier therefor.

The invention further provides a method for prophylaxis and treatment of a retinal disease in a human comprising administering to said human a therapeutically effective amount of a compound of the formula I or a pharmacologically acceptable salt thereof (the compound of the formula I and pharmacologically acceptable salts thereof are hereinafter referred to as "the present compounds").

The invention still further provides a use of one of the present compounds for preparing a pharmaceutical composition for prophylaxis and treatment of a retinal disease in a human.

The retinal disease in a human may, on one hand, be one of the retinal diseases resulting from one or more systemic diseases. Examples of such systemic diseases include diabetes mellitus, hypertension, arteriosclerosis, anemia, leukemia, systemic lupus erythematosus, scleroderma, Tay-Sachs' disease, and Vogt-Spielmeyer disease.

The retinal disease in a human may, on the other hand, be one of the diseases that are localized in the retina. Examples of such diseases localized in the retina include retinopathy of prematurity, retinal vein occlusion, retinal artery occlusion, retinal periphlebitis, retinal detachment, and senile disciform macular degeneration.

The pharmaceutical composition identified above may be in a form of an oral preparation (such as powder, granules, tablets or capsules), an injection or eyedrops.

The compound of the formula I can be prepared according to U.S. Pat. No. 4,564,686 or U.S. Pat. No. 4,914,197, the disclosure of which is incorporated herein by reference.

The present compounds have been known in the art to have a variety of other uses than that disclosed above in this specification. Those known uses in the art are those (a) as an anti-cataract agent, as an agent for prophylaxis and treatment of climacteric disturbance, and for cosmetics with skin-beautifying effect in U.S. Pat. No. 4,564,686; (b) as an antiinflammatory agent in U.S. Pat. No. 4.914,197; (c) as an anti-ulcer agent in U.S. Pat. No. 4,888,329; (d) for prophylaxis and treatment of ischemic disorders in organs in U.S. Pat. No. 4,948,786; (e) as a Maillard reaction inhibitor in EP-A2-0430045 ; and (f) as an antioxidative agent in U.S. Pat. No. 5,306,713.

As noted above, the compound of the formula I can be used for the purpose of the present invention either in its free form as shown by the formula I or in a form of a pharmacologically acceptable salt thereof. Examples of such pharmacologically acceptable salts include alkali metal salts such as sodium salt and potassium salt, and alkaline earth metal salts such as calcium salt and magnesium salt. However, other salts may be used provided that they are pharmacologically acceptable.

The pharmaceutical composition of the present invention may comprise either one or or more of the present compound.

DETAILED DISCUSSION

Figure 1:
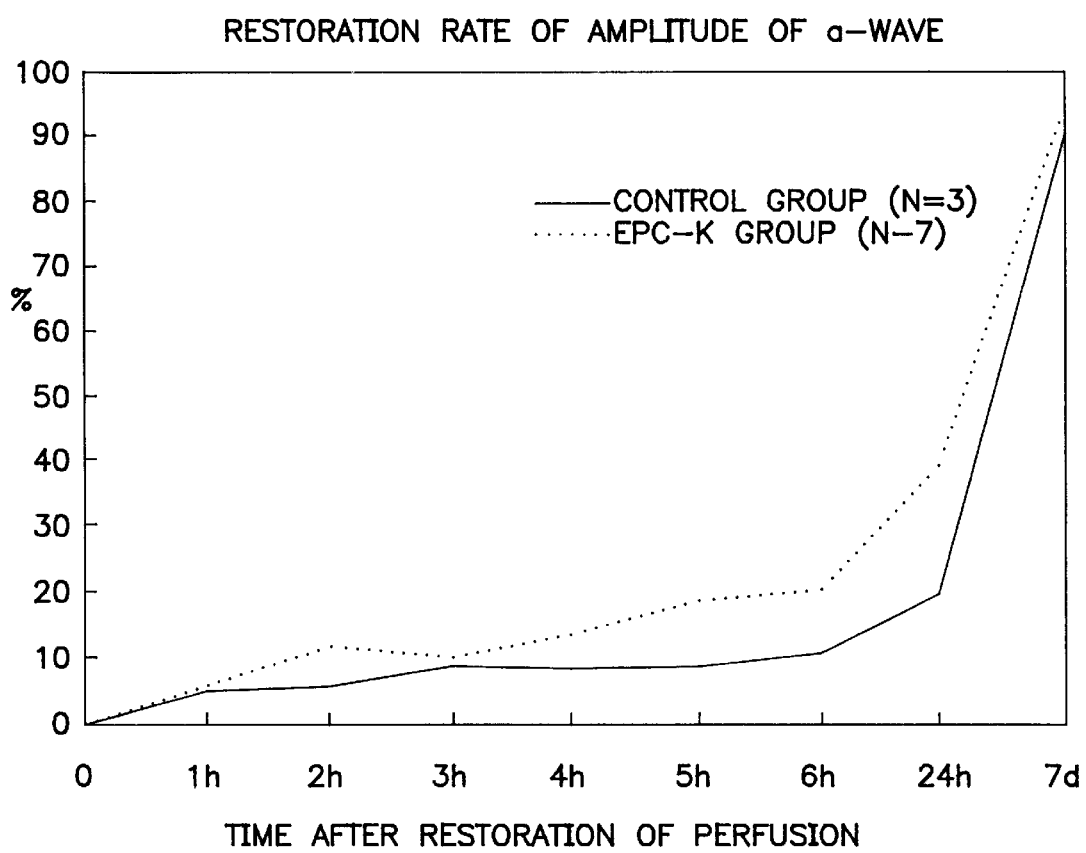
FIG. 1 shows graphically the effect of EPC-K on the restoration of amplitude of the a-wave observed in electroretinogram (ERG) taken in the rats following 45 minutes of retinal ischemia. The horizontal axis represents the time (h=hour, d=day) after restoration of perfusion, and the vertical axis the rate of restoration (%) of the amplitude of the a-wave.

The present compound has a very low toxicity and excels in safety. For example, a potassium salt of one of the compounds represented by the formula I, i.e., potassium salt of a diester of phosphoric acid with L-ascorbic acid and DL-α-tocopherol (hereinafter referred to as "EPC-K"), has $LD_{50}$ values of not less than 5 g/kg p.o. (rat), and not less than 100 mg/kg i.v. (rat). This very low toxicity provides an advantage in using the present compound for the purpose of the present invention.

Retinal diseases which the present invention is usable to prevent and treat include:

(a) vascular disorders and inflammatory or degenerative lesions of the retina resulting from one or more systemic diseases such as diabetes mellitus, hypertension, arteriosclerosis, anemia, leukemia, certain connective tissue diseases (e.g., systemic lupus erythematosus, scleroderma), and some kinds of congenital metabolic abnormalities (e.g., Tay-Sachs' disease, Vogt-Spielmeyer disease,); and (b) diseases localized in the retina including such kinds of retinal vascular disorders (e.g., retinopathy of prematurity, retinal vein occlusion, retinal artery occlusion, and retinal periphlebitis), retinal inflammation or degeneration resulting from retinal detachment or trauma, retinal degenerative diseases accompanying aging (e.g., senile disciform macular degeneration), and congenital retinal degenerative diseases.

The present compound may be used either in a form of oral or non-oral preparation for the purpose of prophylaxis and treatment of retinal diseases. Examples of such preparation form include: eyedrops, eye ointment, tablets, capsules, granules, and injection, all of which can be prepared by conventional methods. Such preparations may, as required, contain conventional additives including excipients, binders, disintegrants, dispersing agents, resorption enhancers, buffers, surfactants, solubilizers, preservatives, emulsifying agents, isotonizers, stabilizers and pH adjusting agents etc.

The doses of the present compound as used for prophylaxis and treatment of retinal diseases will be determined in each case on the basis of the type of retinal disease to be prevented or treated, the age and body weight of the patient, and the symptoms as well as the form of preparation. However, in exemplary embodiments, the doses of the present compound are: approximately 1 to about 100 mg/day/adult (once a day) for injections, approximately 10 to about 1000 mg/once/adult (several times a day) for oral preparations, approximately 0.01 to about 5 w/v % preparation applied several times/day/adult in a few drops each for eyedrops, and approximately 0.01 to about 5 w/w % applied several times/day/adult for eye ointments.

The composition of the present invention may contain other ingredients having pharmacological activity for prophylaxis and treatment of retinal diseases and/or other ingredients having other kinds of pharmacological activities, provided that they do not adversely affect the purpose of the present invention.

Following pharmacological data and examples are presented as a further disclosure and illustration of the present invention and are not intended as a limitation thereof.

PHARMACOLOGY

1. The Effect of the Present Compound on the Changes in Electroretinogram (ERG) in Rat Retinal Ischemia The effect of the present compound was studied on the changes observed in electroretinogram (ERG) using a rat retinal ischemia model that was produced by first elevating the intraocular pressure (abbreviated to "IOP") of the rat to render its ocular tissues ischemic and then resuming perfusion.

Tested Compound: Potassium salt of diester of phosphoric acid with L-ascorbic acid and DL-α-tocopherol (abbreviated to "EPC-K")

Test Method: Seven to nine-week old male SD rats with a body weight of 250 to 340 g, were used as test animals.

The IOP of one eye of each test animal was temporarily elevated, and the resultant lowered retinal function was evaluated by ERG measurement.

Monitoring of IOP: The animals were general anesthetized using urethane (0.7 g/kg, i.v.) and xylazine (2 mg/kg, i.m.). The IOP of the animals was monitored by a pressure transducer connected through a length of polyethylene tubing to a 27 gauge needle inserted into the anterior chamber through the corneal stroma.

IOP Loading: Ocular tissue ischemia was created by elevating IOP to 110 mmHg by introducing a heparinized physiological saline into the anterior chamber over a period of 45 minutes through a 27 gauge needle which was inserted through the corneal stroma into the anterior chamber and which was connected via a length of tubing to a container of the heparinized physiological saline.

Measurement of ERG: Rat ERG was measured before creating ischemia and over time following the restoration of perfusion.

<Measurement condition>

High cut 1 kHz, low cut 1 Hz. Eyes were irradiated by a 0.6 J of xenon light 6 times at 10-second intervals from about 12.5 cm before the cornea, and arithmetic mean values were measured.

Administration: 10 mg/kg of EPC-K (0.25 w/v % in physiological saline) was i.v. administered 10 minutes prior to the end of the ischemic period. Control animals likewise received 4 ml/kg of physiological saline 10 minutes prior to the end of the ischemic period.

Figure 2:
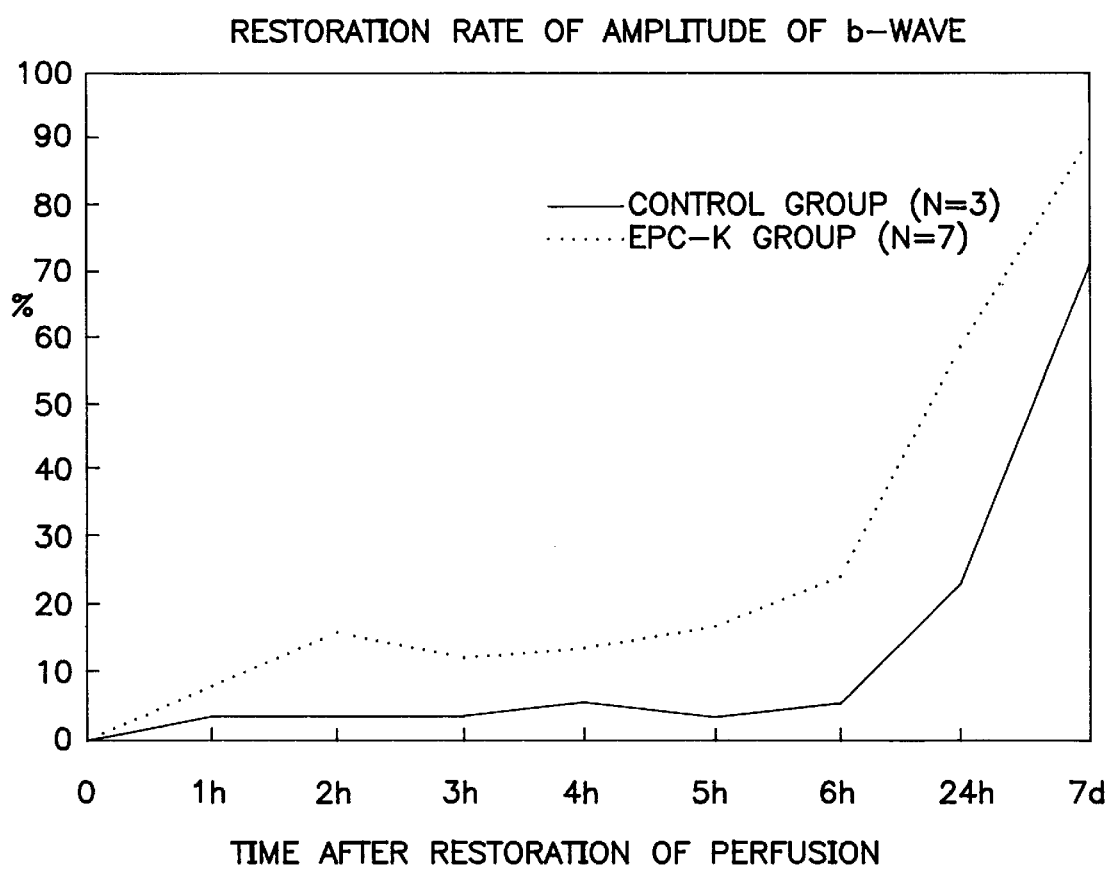
FIG. 2 shows graphically the effect of EPC-K on the restoration of amplitude of the b-wave observed in ERG taken in the rats following 45 minutes of retinal ischemia. The horizontal axis represents the time (h=hour, d=day) after restoration of perfusion, and the vertical axis the rate of restoration (%) of the amplitude of the b-wave.
Figure 3:
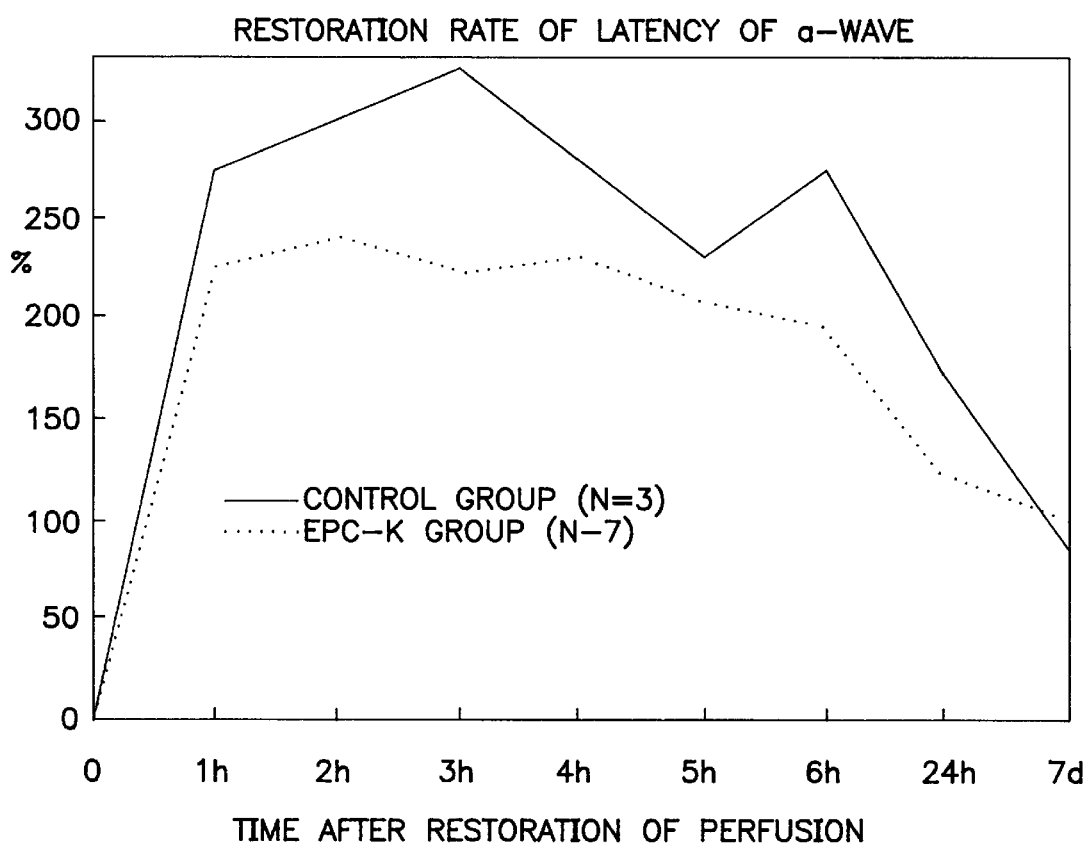
FIG. 3 shows graphically the effect of EPC-K on the restoration of the latency of the a-wave observed in ERG taken in the rats following 45 minutes of retinal ischemia. The horizontal axis represents the time (h=hour, d=day) after the restoration of perfusion, and the vertical axis the rate restoration (%) of the latent time of the a-wave.

Results: FIGS. 1 to 3 show the time profiles of the rate of restoration of amplitude of the a-wave, latency of the a-wave, and amplitude of the b-wave, respectively, for the EPC-K administered group and the control group before creating ischemia and directly after and 1, 2, 3, 4, 5, 6, 24 hours and one week after the restoration of perfusion. The rate of restoration was defined as the rate of a post-ischemia value to the respective pre-ischemia value.

In the both groups, a-wave and b-wave were found lost directly after the restoration of perfusion but became detectable again 1 hour after the restoration of perfusion, and their amplitude gradually increased with the lapse of time. While no difference was found in the latency of the b-waves between the EPC-K administered group and the control, the rate of restoration of amplitude of the a-wave was, as FIG. 1 shows, found to be greater in the EPC-K administered group compared with the control. Also, as FIG. 2 shows, faster restoration of amplitude of the b-wave was noted in the EPC-K administered group compared with the control. Again, as FIG. 3 shows, faster restoration of latency of the a-wave toward 100% value was observed in the EPC-K group compared with the control.

These results demonstrate that the present compound is useful in the treatment of ischemic retinal diseases.

2. Prophylactic Effect of the Present Compound in Rat Retinal Vessel Occlusion Model The present compound was studied for prophylactic effect using retinal vessel occlusion model in the rat.

Test Method: 12-week male SD rats were general anesthetized with Nembutal™ (pentobarbital sodium). The animals (n=8 per group) were i.v. administered 2 ml/kg of EPC-K solution (0.25 w/v % of EPC-K: 5 mg/kg) or physiological saline. Ten minutes later, 2 ml/kg (40 mg/kg) of 2 % rose bengal solution (RB) was i.v. administered. Midriasis was then induced by topical application of MIDORIN P™ (0.5 w/v % tropicamide and 0.5 w/v % phenylephrine hydrochloride: Santen Pharmaceutical Co. Ltd.). After a drop of SCOPISOL™ 15 (1.5 w/v % hydroxyethylcellulose: Senju Pharmaceutical Co. Ltd.) on the cornea, a sheet of slide glass was lightly applied on the cornea and the eye was irradiated by an observation light (175,000 lux) for 2 minutes while observing the ocular fundus through an operation microscope. During the irradiation, severity of blood clot formation within the vessels and vessel occlusion was observed while video tape recording the changes in the retinal vessels. The animals were sacrificed 20 hours after the treatment and specimens for light microscopy were prepared and evaluated pathologically.

Observation of the ocular fundus was carried out on the basis of the following criteria.

<Criteria for evaluation>

0:Normal 0.5:Winding of vessels

1:Formation of spot-like blood clots

2:Blood flow partly blocked

3:Blood flow totally blocked within the irradiated area

Results: 1) Table I shows the results of the fundus observation.

TABLE 1

| Group/No. | 1 | 2 | 3 | 4 | 5 | 6 | 7 | 8 | Mean ± S.D. |
|---|---|---|---|---|---|---|---|---|---|
| Control | 3 | 3 | 2 | 2 | 3 | 3 | 3 | 3 | 2.75 ± 0.46 |
| EPC-K | 1 | 0.5 | 1 | 1 | 1 | 1 | 2 | 1 | 1.06 ± 0.42* |

*Difference from control being significant ($p < 0.01$).

As Table 1 shows, the extent of intra-vascular blood clot formation and vascular occlusion was less severe in the EPC-K administered group compared with the control group which received physiological saline.

2) Pathological Findings

In the irradiated sites in both groups were observed edema of inner layers of the retina (ganglion cell layer, inner plexiform layer, inner nuclear layer), pyknosis of inner and outer nuclear layers, retinal detachment, subretinal exudate, vacuolation and degeneration of inner and outer segments of the visual cells, degeneration of retinal pigment epithelium (RPE), congestion and occlusion of retinochoroidal vessels, disturbances of vascular endothelial cells, and an increased number of inflammatory cells within the vessels. However, the area of the retina where these disorders were noted was smaller in the EPC-K group than the control. Moreover, abnormalities noted in the optic nerve in the control group, i.e., papilledema, optic atrophy, atrophy of and vacuolation around oligodendroglia, were not observed in the EPC-K group.

The above ocular fundus observations and pathological findings demonstrate that the present compound is useful for prophylaxis of retinal diseases caused by ischemia due to, for example, vascular occlusion.

EXAMPLE 1

Oral tablets:

According to a conventional method, an oral tablet having the following formulation is prepared. The tablet may be sugar-coated as required in a conventional method.

| Ingredients | Per tablet |
|---|---|
| EPC-K | 100 mg |
| Lactose | 75 mg |
| Starch | 20 mg |
| Polyethylene glycol 6000 | 5 mg |

EXAMPLE 2

Injection:

According to a conventional method, the following ingredients are mixed to dissolve and the resulting solution is sterilized through filter and aseptically filled into glass ampules 5 ml each, which then are hermetically sealed by heat.

| Ingredients | Per 100 ml |
|---|---|
| EPC-K | 200 mg |
| Mannitol | 5.0 g |
| 1N sodium hydroxide | q.s. to pH 6.5 |
| Distilled water | to total 100 ml |

EXAMPLE 3

Eyedrops:

According to a conventional method, the following ingredients are mixed to dissolve and sterilized through filter to prepare eyedrops.

| Ingredients | Per 100 ml |
|---|---|
| EPC-K | 0.5 g |
| Boric acid | 1.8 g |
| Benzalkonium chloride | 0.005 g |
| 1N sodium hydroxide | q.s. to pH 7.3 |
| Purified sterile water | to total 100 ml |

What is claimed is:

1. A method for treatment of a retinal disease in a human comprising administering to said human a therapeutically effective amount of a compound of the formula I:

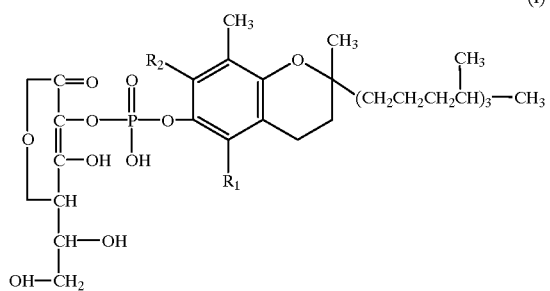

(I)

wherein $R_1$ and $R_2$ independently from each other denote hydrogen or methyl group, or a pharmaceutically acceptable salt thereof and wherein said retinal disease is a disease localized in the retina selected from the group consisting of retinopathy of prematurity, retinal vein occlusion, retinal artery occlusion, retinal periphlebitis and retinal detachment.

2. A method for prophylaxis of a retinal disease in a human comprising selecting a human predisposed to a retinal disease localized in the retina selected from the group consisting of retinopathy of prematurity, retinal vein occlusion, retinal artery occlusion, retinal periphlebitis and retinal detachment and administering to said human a therapeutically effective amount of a compound of the formula I:

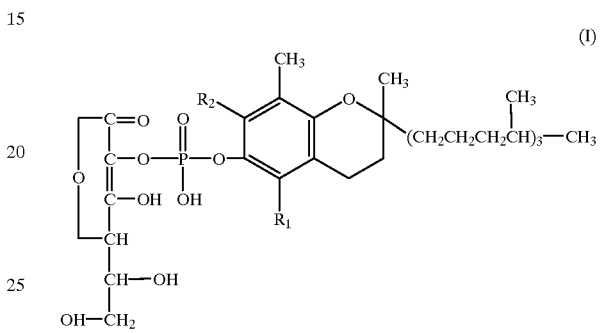

(I)

wherein $R_1$ and $R_2$ independently from each other denote hydrogen or methyl group, or a pharmaceutically acceptable salt thereof.

* * * * *